United States Patent
Kremeier et al.

(10) Patent No.: US 12,420,228 B2
(45) Date of Patent: Sep. 23, 2025

(54) METHOD AND DEVICE FOR SEPARATING CARBON DIOXIDE FROM A RESPIRATORY GAS MIXTURE

(71) Applicant: Loewenstein Medical Technology S.A., Luxembourg (LU)

(72) Inventors: Peter Kremeier, Karlsruhe (DE); Andreas Schober, Frankfurt am Main (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 336 days.

(21) Appl. No.: 18/035,655

(22) PCT Filed: Nov. 2, 2021

(86) PCT No.: PCT/EP2021/025425
§ 371 (c)(1),
(2) Date: May 5, 2023

(87) PCT Pub. No.: WO2022/096147
PCT Pub. Date: May 12, 2022

(65) Prior Publication Data
US 2023/0415094 A1   Dec. 28, 2023

(30) Foreign Application Priority Data
Nov. 9, 2020   (DE) .......................... 102020006856.1

(51) Int. Cl.
*B01D 53/02*   (2006.01)
*A61M 16/00*   (2006.01)
*B01D 53/22*   (2006.01)

(52) U.S. Cl.
CPC ....... *B01D 53/226* (2013.01); *A61M 16/0057* (2013.01); *B01D 2257/504* (2013.01); *B01D 2257/708* (2013.01); *B01D 2259/4533* (2013.01)

(58) Field of Classification Search
CPC .......... A61M 16/0057; A61M 16/0066; A61M 16/0093; A61M 16/01; A61M 16/024; A61M 16/0891; A61M 16/202; A61M 16/208; A61M 16/22; A61M 2016/003; A61M 2016/1025; A61M 2016/103; A61M 2016/1035; A61M 2202/0208; A61M 2202/0225; A61M 2202/0241; A61M 2205/3334; A61M 2230/432; B01D 2257/504; B01D 2257/708; B01D 2258/06; B01D 2259/4533; B01D 53/226; Y02C 20/40
See application file for complete search history.

(56) References Cited

U.S. PATENT DOCUMENTS

| | | | |
|---|---|---|---|
| 5,102,432 A * | 4/1992 | Prasad ................. | C01B 21/045 96/9 |
| 6,168,649 B1 | 1/2001 | Jensvold et al. | |
| 7,604,681 B2 * | 10/2009 | Malsam ................ | B01D 71/44 95/47 |
| 8,419,828 B2 * | 4/2013 | Diaz ....................... | C10L 3/12 96/9 |

(Continued)

*Primary Examiner* — Christopher P Jones
(74) *Attorney, Agent, or Firm* — Abel Schillinger, LLP (57) ABSTRACT

The invention relates to a method and a device for separating carbon dioxide from a respiratory gas mixture. The separation is carried out by means of a membrane which acts as a molecule filter.

18 Claims, 3 Drawing Sheets

(56) References Cited

U.S. PATENT DOCUMENTS

| | | | |
|---|---|---|---|
| 10,076,620 B2 * | 9/2018 | Schmidt | A61M 16/104 |
| 10,201,778 B2 * | 2/2019 | Gu | B01D 53/1425 |
| 10,258,921 B2 * | 4/2019 | Fukuda | B01D 53/226 |
| 10,471,380 B2 * | 11/2019 | Priske | B01D 53/225 |
| 10,561,978 B2 * | 2/2020 | Jensvold | B01D 69/08 |
| 10,569,217 B2 * | 2/2020 | Mitariten | C07C 7/005 |
| 11,471,823 B2 * | 10/2022 | Roodbeen | B01D 53/227 |
| 2009/0126733 A1 | 5/2009 | Kulkarni et al. | |
| 2014/0174438 A1 | 6/2014 | Schmidt et al. | |

* cited by examiner

METHOD AND DEVICE FOR SEPARATING CARBON DIOXIDE FROM A RESPIRATORY GAS MIXTURE

BACKGROUND OF THE INVENTION

1. Field of the Invention

The invention relates to a method and device for removing at least carbon dioxide ($CO_2$) from a respiratory gas mixture. The separation is carried out, for example, with the aid of a membrane acting as a molecular filter.

2. Discussion of Background Information

The removal of $CO_2$ from carbon dioxide-containing gas mixtures, as occur in ventilation or anesthesia, is a demanding task.

It is known that the respiratory gases administered circulate in a closed circuit for reasons of economy and safety, with oxygen and/or $CO_2$ and/or anesthetic gases being replenished depending on consumption and carbon dioxide being withdrawn from the circuit. In general, an accumulation of carbon dioxide in ventilation systems should be avoided. A limit value that should not be exceeded is usually a concentration value of 0.5%.

The amount of carbon dioxide that needs to be removed depends on the individual application. Exhaled air contains about 5% carbon dioxide. This concentration should be reduced to a value of 0.5% or less in the breathing circuit.

$CO_2$ is customarily bound to soda lime and thus withdrawn from the circuit. However, soda lime is not reusable and must be disposed of.

It is therefore an object of the invention to provide a cost-effective and practicable way of removing specific respiratory gases. It is also an object of the invention to provide regulation of the proportions of specific respiratory gas concentrations in a respiratory gas mixture.

SUMMARY OF THE INVENTION

The invention comprises a method for separating a respiratory gas mixture which contains at least $O_2$ and $CO_2$ and at least one volatile anesthetic and flows in a respiratory gas path in which the respiratory gas mixture is guided under a first flow to a first separation material, wherein the first separation material separates at least oxygen $O_2$ and carbon dioxide $CO_2$ from the at least one volatile anesthetic and wherein the at least one volatile anesthetic is returned to the respiratory gas path or remains in the respiratory gas system, wherein the removed remaining respiratory gas mixture containing at least oxygen $O_2$ and carbon dioxide $CO_2$ is guided under a second flow to a second separation material, wherein the second separation material separates at least carbon dioxide $CO_2$ from the respiratory gas mixture and wherein the removed carbon dioxide $CO_2$ is segregated at least temporarily or released into the environment or into a respiratory gas scavenging system and wherein the remaining portion of the respiratory gas mixture, namely essentially oxygen $O_2$, is returned to the first separation material.

The method is additionally also characterized in that the first separation material selectively allows the smaller molecules oxygen $O_2$ and carbon dioxide $CO_2$ to pass through and retains at least one volatile anesthetic.

The method is additionally also characterized in that the first separation material is a diffusion filter.

The method is additionally also characterized in that the respiratory gases are separated across the diffusion filter owing to a concentration gradient.

The method is additionally also characterized in that the second separation material is a diffusion filter.

Alternatively or additionally, the invention relates to a method (or a device) in which the second separation material selectively allows the smaller molecules nitrogen $N_2$ and/or oxygen $O_2$ to pass through and at least largely retains at least carbon dioxide $CO_2$.

The method is additionally also characterized in that the second separation material is a diffusion filter which has a permeability ratio of $N_2$ and/or $O_2$ to $CO_2$ of at least 50:1.

The method is additionally also characterized in that the second separation material is a diffusion filter which has a permeability ratio of $N_2$ and/or $O_2$ to $CO_2$ of at least 100:1.

The method is moreover also characterized in that the first flow is 4 to 25 l/min.

The method is also characterized in that the first flow is 3 to 18 l/min.

The method is additionally also characterized in that the first flow is generated by a fan or a pressurized gas source or a pump.

The method is also characterized in that the first flow contains, at least in phases, respiratory gas containing 10% to 30% oxygen.

The method is in addition characterized in that the second flow is 4 to 25 l/min.

The method is additionally also characterized in that the second flow is 6 to 18 l/min.

The method is also characterized in that the second separation material is a diffusion filter which has a permeability ratio of $O_2$ to $CO_2$ of preferably such a size that the flow of $CO_2$ released into the environment or into a respiratory gas scavenging system is lower than the flush flow of the first separation material.

The method is also distinguished in that the second flow is generated by a fan or a pressurized gas source or a pump.

The method is additionally also characterized in that the respiratory gas mixture is at least partially or fully withdrawn from the expiratory respiratory gas path.

The method is also characterized in that first separation material is respiratory gas-conductingly connected via a first exit to an inspiratory respiratory gas path, wherein a respiratory gas source is disposed downstream of the first separation material and upstream of the inspiratory patient port.

The method is additionally also characterized in that a fresh gas supply (of oxygen) and an anesthetic gas supply are disposed downstream of the first separation material and upstream of the respiratory gas source.

The method is moreover also characterized in that an oxygen sensor and/or a flow sensor and/or a $CO_2$ sensor is/are disposed downstream of the respiratory gas source.

The method is also characterized in that the respiratory gas mixture comprises at least nitrogen $N_2$, oxygen $O_2$, carbon dioxide $CO_2$ and at least one volatile anesthetic.

The method also allows regulation of the proportions of specific respiratory gases in a respiratory gas mixture. For this purpose, a feed or supply line of respiratory gases—in particular of $O_2$, $CO_2$ and/or anesthetic gas—is provided according to the invention. The removal or clearance of at least proportions of specific respiratory gases from a respiratory gas mixture is also provided. The acts of regulation necessary therefor, in particular the control of the necessary actuators, are performed by a control unit, which can also be divided into multiple sub-control units.

The invention also relates to a device for separating a respiratory gas mixture which contains at least O2 and CO2 and at least one volatile anesthetic and flows in a respiratory gas path in which the respiratory gas mixture is guided under a first flow to a first separation material, wherein the first separation material separates at least oxygen O2 and carbon dioxide CO2 from the at least one volatile anesthetic and wherein the at least one volatile anesthetic is returned to the respiratory gas path or remains in the respiratory gas system, wherein the removed remaining respiratory gas mixture containing at least oxygen O2 and carbon dioxide CO2 is guided under a second flow to a second separation material, wherein the second separation material separates at least carbon dioxide CO2 from the respiratory gas mixture and wherein the removed carbon dioxide CO2 is segregated at least temporarily or released into the environment or into a respiratory gas scavenging system and wherein the remaining portion of the respiratory gas mixture, namely essentially oxygen O2, is returned to the first separation material.

The device is optionally also characterized in that the respiratory gas mixture is directly or forcedly conducted to the separation material by the patient or by means of a pump or turbine, wherein the first separation material is arranged and configured to separate at least oxygen O2 and/or carbon dioxide CO2 from at least one volatile anesthetic, wherein the at least one volatile anesthetic is returned to the respiratory gas path or remains in the respiratory gas path, wherein the respiratory gas path comprises a respiratory gas pump (which can be a valve or a turbine or a respiratory gas source) and wherein the respiratory gas is conducted to the patient via a patient interface.

The device is optionally also characterized in that the first separation material can be in the form of a diffusion filter in one branch of a respiratory gas tube or be in the form of a filter housing having an inlet for respiratory gas, an upper chamber, an outlet for respiratory gas to the patient, a diffusion filter, a lower chamber and an outlet for respiratory gas from the lower chamber, to the respiratory gas path in the direction of the second separation material, and an inlet into the lower chamber, coming from the line from the second separation material.

The device is also characterized in that the removed remaining respiratory gas mixture (containing at least nitrogen N2 and oxygen O2 and carbon dioxide CO2) is guided under a second flow via a line to a second separation material and the second separation material separates at least carbon dioxide CO2 from the respiratory gas mixture, wherein the removed carbon dioxide CO2 is segregated at least temporarily or released into the environment or into a respiratory gas scavenging system, wherein means which regulate the flow of the removed carbon dioxide are present.

The device is moreover also characterized in that the remaining portion of the respiratory gas mixture, namely essentially (nitrogen N2 and) oxygen O2, is returned via the line to the first separation material, wherein, for this purpose, a respiratory gas pump/turbine which generates the necessary flush flow (which can also simply be a volume displacement) of the respiratory gas is disposed in the line or gas-conductingly connected to the line.

The device is also characterized in that a check valve which selectively prevents a flow of respiratory gas in one direction is disposed in the line between the first separation material and the second separation material.

According to the invention, the separation material 1 and 2 are configured identically or differently. This applies in particular to the choice of filters. For example, the filters have different selectivity for oxygen and carbon dioxide and/or anesthetics.

The device is additionally also characterized in that the second separation material is in the form of a filter having an upper part and a lower part, wherein a diffusion filter is disposed between the parts, wherein the upper part has an inflow for the respiratory gas mixture (which comes from the first separation material) and an outflow to the environment, wherein the lower part has an outflow to the respiratory gas path in the direction of the first separation material, wherein a pump/turbine which generates the flush flow for the respiratory gas is disposed in the respiratory gas path between the outflow and the inflow.

The device is optionally also characterized in that the diffusion filter is steam-sterilizable, i.e., is thermally stable up to 134° C.

The device is optionally also characterized in that both diffusion filters and are in the form of film filters/surface filters or in the form of tubes (hollow fibers), wherein the size of the surfaces and of the passage cross-sections are configured in such a way that a flow of 60 l/min is possible in the direction of flow and a maximum pressure drop of 2 cmH2O (==mbar, ==hPa) is not exceeded in the direction of flow and/or diffusion.

The device is optionally also characterized in that the permeability ratio of N2 and/or O2 to CO2 of the diffusion filter is configured in such a way that CO2 is substantially retained, wherein the permeability ratio is preferably of such a size that the flow of CO2 released into the environment or into a respiratory gas scavenging system is lower than the flush flow in the first stage with the separation material.

The device is also characterized in that the first flow into the separation material is 4 to 30 l/min and the second flow into the separation material is 1 to 35 l/min.

The device is optionally also characterized in that the flush flow between first chamber and subsequent chamber can be regulated according to the requirements, with the result that the CO2 content leaving the first stage is adjustable.

The device is also characterized in that a respiratory gas pump is disposed downstream of the first separation material and upstream of the inspiratory patient port.

The device is optionally also characterized in that a fresh gas supply (of oxygen) and/or an anesthetic gas supply is/are disposed downstream of the first separation material and upstream of the respiratory gas pump.

The device is also characterized in that an oxygen sensor and/or flow sensor and/or CO2 sensor is/are disposed downstream of the respiratory gas pump.

The device is optionally also characterized in that a cascaded flush-flow treatment through the separation material is provided, in which the second separation material is in the form of a double or multiple diffusion filter.

The device is also characterized in that the second separation material separates at least carbon dioxide CO2 from the respiratory gas mixture and segregates it out of the upper chamber via the exit into the respiratory gas scavenging system, wherein a pump returns the segregated carbon dioxide CO2 via a line to the entrance of the second separation material.

The device is also characterized in that the remaining portion of the respiratory gas mixture that has diffused through the diffusion filter, namely essentially nitrogen N2 and oxygen O2, which still comprises here 6% CO2 for example, is conducted from the lower chamber through the opening to the second separation material and enters here through the intake.

The device is also characterized in that the intake of the second filter is fed by the outlet of the first filter, wherein a further reduced proportion of CO2 thus predominates in the lower part of the second separation material and wherein the respiratory gas treated in this way is returned to the first separation material.

The invention also comprises a tubing system having a device according to the invention.

The invention also comprises a ventilator having a device according to the invention.

The invention also comprises a ventilator arranged and configured to carry out the steps of the method.

The invention also comprises a ventilator comprising a device for separating a respiratory gas mixture which contains at least O2 and CO2 and flows in a respiratory gas path
  in which the respiratory gas mixture is guided under a first flow to a first separation material,
  wherein the first separation material separates at least oxygen O2 and carbon dioxide CO2 and
  wherein oxygen and a reduced proportion of CO2 are returned to the respiratory gas path or remain in the respiratory gas system
  wherein the removed remaining respiratory gas mixture containing at least oxygen and an increased proportion of carbon dioxide CO2 is guided under a second flow to a second separation material,
  wherein the second separation material separates at least carbon dioxide CO2 from the respiratory gas mixture and
  wherein the removed carbon dioxide CO2 is segregated at least temporarily or released into the environment or into a respiratory gas scavenging system and
  wherein the remaining portion of the respiratory gas mixture, namely essentially oxygen O2 and a reduced proportion of CO2, is returned to the first separation material.

Alternatively or additionally, the invention consists of a method and device for separating CO2 from a respiratory gas mixture, in which the respiratory gas mixture is guided along one side of a specific semipermeable membrane through which transfer of the components of the gas mixture can occur, wherein the membrane is chosen such that the transfer of CO2 and/or at least one volatile anesthetic through the membrane occurs substantially less effectively than the transfer of the other gas components of the respiratory gas mixture, wherein two membranes are used.

It should be noted that the features presented individually in the claims can be combined with one another in any technically meaningful way and they indicate further embodiments of the invention. The description provides additional characterization and specification of the invention, especially in connection with the figures.

It should be further noted that an "and/or" conjunction that is used herein and that is between two features and links them together is always to be interpreted as meaning that only the first feature can be present in a first embodiment of the subject matter according to the invention, only the second feature can be present in a second embodiment, and both the first and the second feature can be present in a third embodiment.

The dependent claims relate to various mutually independent advantageous developments of the present invention, the features of which can be combined freely with one another by a person skilled in the art within the scope of what is technically meaningful. In particular, this also applies beyond the boundaries of the various claim categories.

In the context of the invention, a respiratory gas mixture is any breathable gas mixture containing oxygen O2 and carbon dioxide (CO2) and/or at least nitrogen N2 and/or at least one anesthetic gas (e.g., sevoflurane, desflurane, nitrous oxide, xenon . . . ).

The filters used according to the invention are chemically resistant to the gases and vapors used. The filter module as a whole is arranged and configured in such a way that it can be cleaned and/or sterilized. The filters or the filter module therefore have the necessary temperature resistance of at least 134° C.

It is particularly advantageous if a number of methods for reducing the partial pressure of CO2 or the proportion of CO2 are combined with one another, i.e., the partial pressure of CO2 is adjusted by gas flushing on the side of the membrane facing away from the respiratory gas mixture and by lowering the total pressure on the side of the membrane facing away from the respiratory gas mixture.

A major advantage of the membranes used is especially that they are highly resistant to halogenated hydrocarbons. For this reason, they are particularly suitable for long-term applications in anesthesia or ventilation systems in which significant exposure to these substances is to be expected.

According to the invention, sensors can be used to provide information about the respiratory gas values or parameters, for example about carbon dioxide.

According to the invention, ventilators are noninvasive devices for domestic applications or invasive clinical ventilators or anesthetic ventilators and are thus, in each case, devices or applications in which carbon dioxide may be an important guiding parameter for the success of the ventilation or the state of the patient.

DETAILED DESCRIPTION OF EMBODIMENTS OF THE INVENTION

Figure 1:
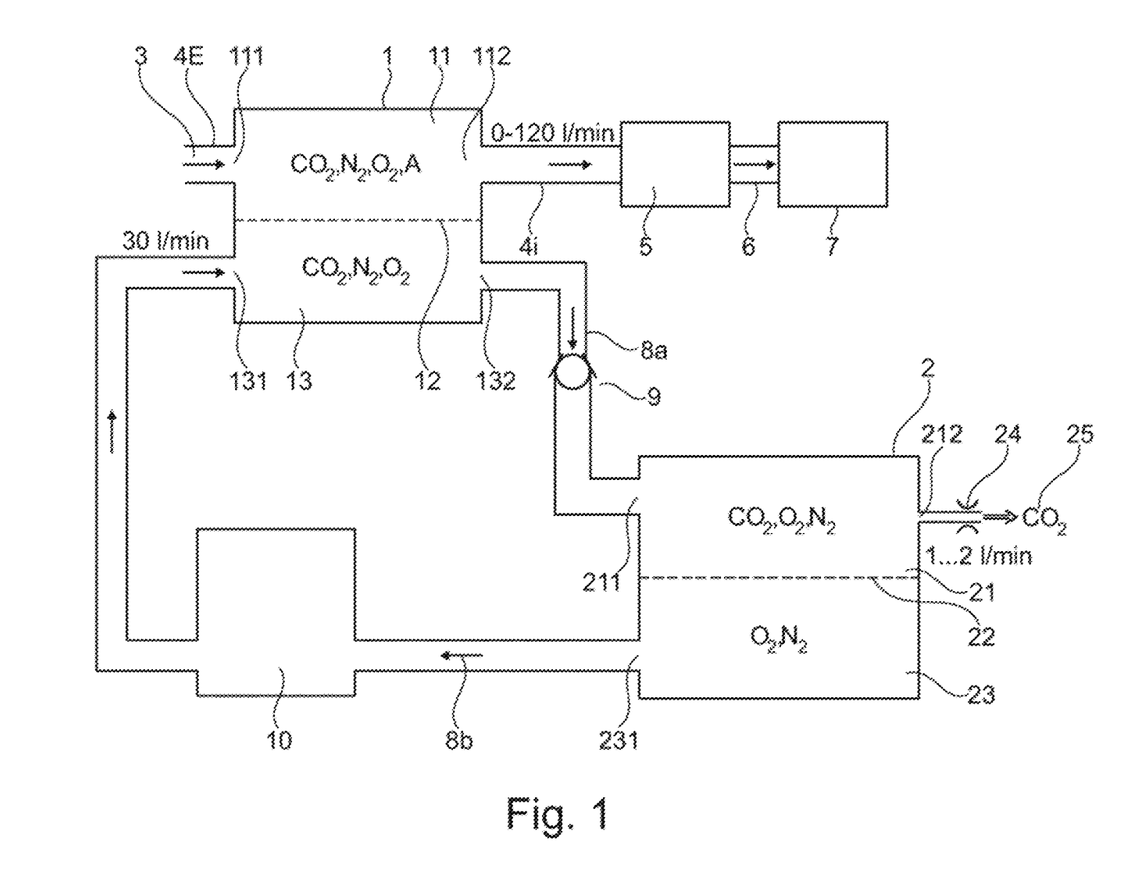
FIG. 1 schematically shows a device according to the invention and a corresponding method for separating a respiratory gas mixture.

FIG. 1 shows a device according to the invention and the method for separating a respiratory gas mixture 3. The respiratory gas mixture 3 contains at least oxygen O2 and carbon dioxide CO2 and optionally nitrogen N2 and/or at least one volatile anesthetic.

The respiratory gas mixture 3 flows through a respiratory gas path 4 and is guided under a first flow to a first separation material 1. The respiratory gas mixture 3 flows through the respiratory gas path 4 at least sectionally through at least one line 8. The line 8 can at least be divided into a line 8a and a line 8b. The respiratory gas mixture 3 is brought to the separation material 1 directly or forcedly (by the patient or by means of a pump or turbine).

The first separation material 1 is arranged and configured to separate at least oxygen O2 and/or carbon dioxide CO2 from at least one volatile anesthetic (A).

The at least one volatile anesthetic is returned to the respiratory gas path 4 or remains in the respiratory gas path 4. The respiratory gas path 4 comprises a respiratory gas pump 5 (which can be a valve or a turbine or a respiratory gas source), which can be in the form of a turbine. The respiratory gas is conducted to the patient 7 via a patient interface 6.

The first separation material 1 can be merely a diffusion filter in one branch (e.g., the expiratory branch) of a respiratory gas tube or the separation material 1 can be in the form of a filter housing having an inlet 111 for respiratory gas, an upper chamber 11, an outlet 112 for respiratory gas to the patient, a diffusion filter 12, a lower chamber 13 and an outlet 132 for respiratory gas from the lower chamber 13 and an inlet into the lower chamber 131.

The removed remaining respiratory gas mixture (containing at least nitrogen N2 and oxygen O2 and carbon dioxide CO2) is guided under a second flow via the line 8a to a second separation material 2. The second separation material 2 separates at least carbon dioxide CO2 from the respiratory gas mixture. The removed carbon dioxide CO2 is segregated at least temporarily or released into the environment 25 or into a respiratory gas scavenging system 25.

Means 24 which regulate the flow of the removed carbon dioxide are present.

The remaining portion of the respiratory gas mixture, namely essentially (nitrogen N2 and) oxygen O2, is returned via the line 8b to the first separation material 1. For this purpose, a respiratory gas pump/turbine 10 which generates the necessary flush flow (which can also simply be a volume displacement) of the respiratory gas is disposed in the line 8b or gas-conductingly connected to the line 8a and/or 8b. A check valve 9 which selectively prevents a flow of respiratory gas in one direction, namely in particular a flow from the second separation material 2 to the first separation material 1, can be disposed in the line 8a between the first separation material 1 and the second separation material 2.

The first separation material 1 is arranged and configured to selectively allow the smaller molecules nitrogen N2, oxygen O2 and carbon dioxide CO2 to pass through and retain larger molecules such as a volatile anesthetic. Here, the first separation material 1 is in the form of a filter having an upper part 11 and a lower part 13, wherein a diffusion filter 12 is disposed between the parts. The upper part 11 has an inflow 111 for the respiratory gas mixture 3 and an outflow 112 to the respiratory gas path 4 in the direction of a patient 7.

The lower part 13 has an inflow 131 and an outflow 132 to the respiratory gas path 8a in the direction of the second separation material 2. The second separation material is arranged to selectively allow the smaller molecules nitrogen N2 and oxygen O2 to pass through and at least largely retain at least carbon dioxide CO2. The second separation material 2 can comprise a diffusion filter 22.

Here, the second separation material 2 is in the form of a filter having an upper part 21 and a lower part 23, wherein a diffusion filter 22 is disposed between the parts. The upper part 21 has an inflow 211 for the respiratory gas mixture 3 (which comes from the first separation material) and an outflow 212 to the environment 25.

The lower part 23 has an outflow 231 to the respiratory gas path 8b in the direction of the first separation material 1. A pump/turbine 10 which generates the flush flow for the respiratory gas is disposed in the respiratory gas path between the outflow 231 and the inflow 131. A narrowing 24 which regulates the flow of CO2-containing respiratory gas is disposed between the outflow 212 and the environment. The respiratory gases are separated across the diffusion filter 12, 22 owing to a concentration gradient.

The first separation material 1 comprises, for example, a diffusion filter 12. The diffusion filter 12 is contaminated with patient gases (at least the upper chamber 11) and should therefore be reprocessable (sterilizable, washable). The diffusion filter 12 should be steam-sterilizable, i.e., thermally stable up to 134° C. Chemical absorbers of today are used up after a relatively short time (e.g., a work shift of 4-10 hours) and are then hazardous waste because they then contain chlorofluorocarbons (volatile anesthetics). A diffusion filter would therefore have to withstand around 50 autoclave cycles if used for one year and reprocessed weekly. Both diffusion filters 12 and 22 are in the form of film filters/surface filters or in the form of tubes (hollow fibers). The size of the surfaces and of the passage cross-sections are configured in such a way that a flow of 60 l/min is possible in the direction of flow and a maximum pressure drop of 2 cmH2O (=mbar, =hPa) is not exceeded in the direction of flow and/or diffusion. If necessary, many films or many hollow fibers can be parallelized.

Diffusion filters 12, 22 can be produced from various plastics, ceramics, pressed glass beads, or sintered or rolled metals (or combinations thereof). Commonly used are polysulfones, polyethersulfone (PES), cellulose, cellulose esters (cellulose acetate, cellulose nitrate), regenerated cellulose (RC), silicones, polyamides ("nylon", more precisely: PA 6, PA 6.6, PA 6.10, PA 6.12, PA 11, PA 12), polyamideimide, polyamide urea, polycarbonates, ceramic, stainless steel, silver, silicon, zeolites (aluminosilicates), polyacrylonitrile (PAN), polyethylene (PE), polypropylene (PP), polytetrafluoroethylene (PTFE), polyvinylidene fluoride (PVDF), polyvinyl chloride (PVC), polypiperazineamide.

Combinations of these materials are used to produce thin film ("TF") membranes, commonly composed of a support layer (e.g., cellulose acetate) and a coating (e.g., polyamide).

The second separation material 22 is arranged to selectively allow the smaller molecules nitrogen N2 and oxygen O2 to pass through and at least largely retain at least carbon dioxide CO2. The second separation material 2 comprises a diffusion filter 22. The permeability ratio of N2 and O2 to CO2 of the diffusion filter 22 is at least 50:1. The permeability ratio of N2 and O2 to CO2 can also be at least 100:1. The permeability ratio should preferably be of such a size that, after the 2nd stage, the flow of CO2 released into the environment or into a respiratory gas scavenging system 25 is lower than the flush flow in the first stage (separation material 1).

The first flow into the separation material 1 is, for example, 4 to 25 l/min or 6 to 18 l/min. The released flow should be as low as possible. The released flow should be lower than the typical mean expiratory patient flow as far as possible.

An adult patient exhales on average less than 8 liters of respiratory gas per minute, containing <=5% CO2 on average. If the gas in the diffusion filter 2 can be enriched by a factor of 10 to 12, the flow rate for the released flow (through 212) is 0.6 to 0.8 l/min, which is acceptable.

The first flow is generated by a fan or a pressurized gas source or a pump 5, or the patient breathes directly into the separation material 1, for example when the separation material 1 is in the expiratory tube. In this example, the respiratory gas path 4 is the expiratory respiratory gas path 4e.

The second flow into the separation material 2 is 1 to 25 l/min or 6 to 18 l/min. The flush flow between chamber 13 and the upper chamber 21 and the lower chamber 23 can be regulated according to the requirements. As a result, it would be possible to adjust the CO2 content leaving the first stage at 132. Although a higher CO2 content at the exit of the first stage (at 132) is not ideal for the patient, it could conserve power and extend operating time with battery operation.

The second flow is generated by a fan or a pressurized gas source or a pump 10. The respiratory gas mixture 3 is at least partially or fully withdrawn from the expiratory respiratory gas path 4e. The first separation material 1 is respiratory gas-conductingly connected via a first exit 112 to an inspiratory respiratory gas path 4i, wherein a respiratory gas pump 5 is disposed downstream of the first separation material 1 and upstream of the inspiratory patient port 6. Optionally, a fresh gas supply (of oxygen) and an anesthetic gas supply are disposed downstream of the first separation material 1 and upstream of the respiratory gas pump 5. Optionally, a sensor, in particular an oxygen sensor and/or anesthetic gas sensor, is disposed downstream of the respiratory gas pump 5. Optionally, a flow sensor is disposed downstream of the respiratory gas pump 5. Optionally, a CO2 sensor (capnometry) is disposed downstream of the respiratory gas pump 5. Sensors can moreover be disposed in the respiratory gas path before the first separation material 1 and/or after the first separation material 1. Sensors can also be disposed in the respiratory gas path before the second separation material 2 and/or after the second separation material 2.

The method and the device also allow regulation/control of the proportions of specific respiratory gases in a respiratory gas mixture. For this purpose, a feed or supply line of respiratory gases—in particular of O2, CO2 and/or anesthetic gas—is provided according to the invention. The removal or clearance of at least proportions of specific respiratory gases from a respiratory gas mixture is also provided. The acts of regulation necessary therefor, in particular the control of the necessary actuators, are performed by a control unit, which can also be divided into multiple sub-control units.

In particular, what are controlled/regulated are the actuators, namely in particular the pump/turbine 5, 10, 26 for controlling the flows, the means 24 for clearing (proportions of) respiratory gas, check valves 9, the fresh gas supply (of oxygen) and the anesthetic gas supply.

For the regulation/control of the proportions of specific respiratory gases in a respiratory gas mixture, the control unit takes account of user specifications and/or stored instructions and/or the sensor signals. In particular of at least one flow sensor and/or CO2 sensor and/or O2 sensor and/or anesthetic gas sensor.

Figure 2:
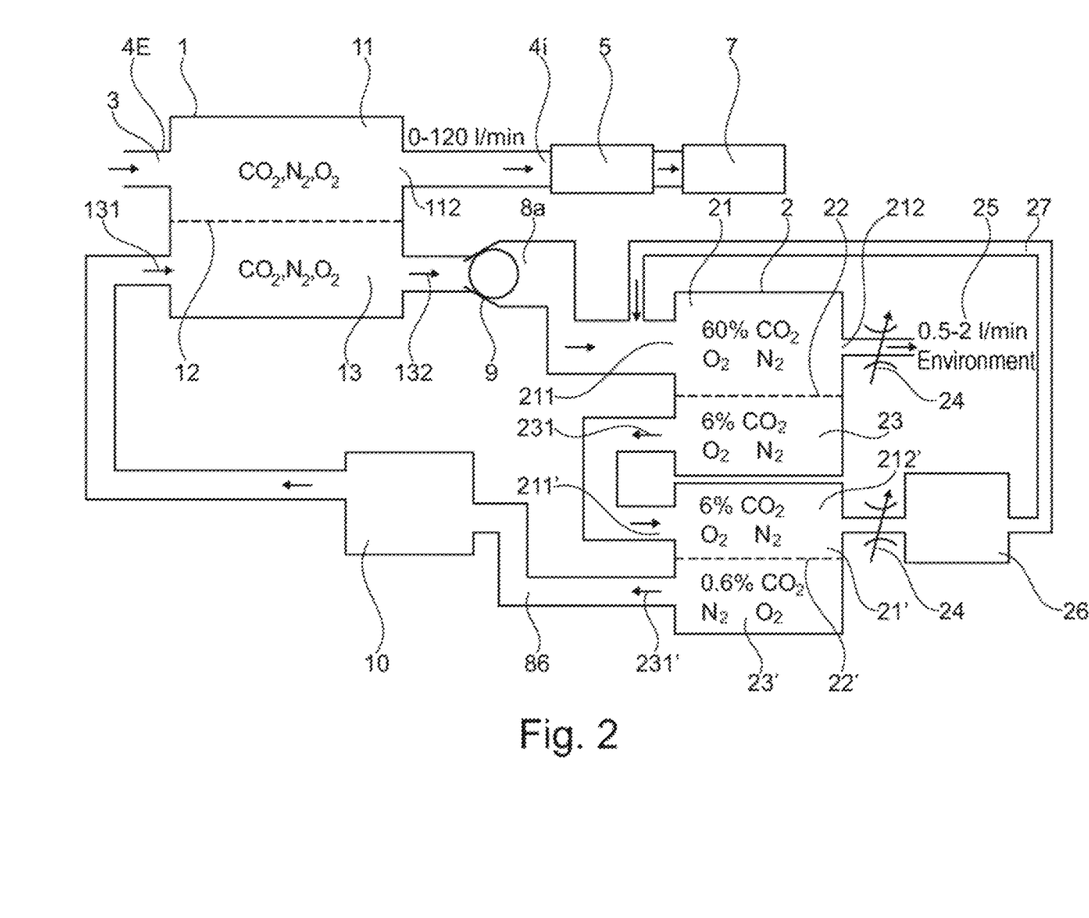
FIG. 2 schematically shows another device according to the invention and a corresponding method for separating a respiratory gas mixture.

FIG. 2 shows a device according to the invention and the method for separating a respiratory gas mixture 3. The respiratory gas mixture contains at least oxygen O2 and carbon dioxide CO2 and optionally nitrogen N2 and/or at least one volatile anesthetic (A). FIG. 2 shows the device according to FIG. 1, but with a cascaded flush-flow treatment through the separation material 2. This could be used in the event of the diffusion coefficient being distinctly smaller than 100 or if the gas loss is to be reduced even further. Theoretically, any number of stages cascade. Each stage requires one pump. However, since the flows are very small, the pumps can also be small and cost-effective. As a result, it is possible via a cascaded flush-flow treatment to release a small amount of gas enriched with high concentrations of CO2.

The remaining respiratory gas mixture removed after passing through the first diffusion filter 12 and containing at least oxygen O2 and carbon dioxide CO2, which comprises here 60% CO2 for example, is guided under a second flow via a line 8a to a second separation material 2. The second separation material is arranged to selectively allow the smaller molecules nitrogen N2 and oxygen O2 to pass through and at least largely retain at least carbon dioxide CO2. The second separation material 2 is in the form of a double or multiple diffusion filter 2.

The second separation material 2 separates at least carbon dioxide CO2 from the respiratory gas mixture and segregates it out of the upper chamber 21 via the exit 212. The removed carbon dioxide CO2 is segregated at least temporarily or released into the environment 25 or into a respiratory gas scavenging system 25. The respiratory gas scavenging system 25 optionally comprises a pump 26 which returns the removed carbon dioxide CO2 to the entrance 211 of the second separation material 2 via a line 27.

The remaining portion of the respiratory gas mixture that has diffused through the diffusion filter 22, namely essentially nitrogen N2 and oxygen O2, which still comprises here 6% CO2 for example, is conducted from the lower chamber 23 through the opening 231 to the second separation material 2' and enters through the intake 211'.

The first filter has an upper part 21 and a lower part 23, wherein a diffusion filter 22 is disposed between the parts. The upper part 21 has an inflow 211 for the respiratory gas mixture 3 and an outflow 212 to the environment 25. A narrowing 24 which regulates the flow of CO2-containing respiratory gas is disposed between the outflow 212 and the environment.

The lower part 23 has an outflow 231 in the direction of the second filter 2'.

The inlet 211' of the second filter 2' is fed by the outlet of the first filter 231. The upper part 21' has an outflow 212' to a pump 26, which conducts CO2-containing respiratory gas (containing 6% CO2) via a line 27 to the inlet 211 of the first filter 2. In the lower part 23' of the second separation material 2', the proportion of CO2 is therefore reduced to 0.6% in this example. The respiratory gas treated in this way is returned to the first separation material 1.

A respiratory gas pump 10 which generates the flush flow for the respiratory gas is disposed in the respiratory gas path between the outflow 231' of the second filter and the inflow 131 of the first filter.

In line with the embodiment of FIG. 1, it is also possible in the case of the embodiment according to FIG. 2 to dispose a respiratory gas pump 5 downstream of the first separation material 1 and upstream of the inspiratory patient port 6. Optionally, a fresh gas supply (of oxygen) and an anesthetic gas supply are disposed downstream of the first separation material 1 and upstream of the respiratory gas pump 5. Optionally, a sensor, in particular an oxygen sensor and/or anesthetic gas sensor, is disposed downstream of the respiratory gas pump 5. Optionally, a flow sensor is disposed downstream of the respiratory gas pump 5. Optionally, a CO2 sensor (capnometry) is disposed downstream of the respiratory gas pump 5. Sensors can moreover be disposed in the respiratory gas path before the first separation material 1 and/or after the first separation material 1. Sensors can also be disposed in the respiratory gas path before the second separation material 2 and/or after the second separation material 2, or also in the line 27.

The method and the device also allow regulation/control of the proportions of specific respiratory gases in a respiratory gas mixture. For this purpose, a feed or supply line of respiratory gases—in particular of O2, CO2 and/or anesthetic gas—is provided according to the invention. The removal or clearance of at least proportions of specific respiratory gases from a respiratory gas mixture is also provided. The acts of regulation necessary therefor, in particular the control of the necessary actuators, are performed by a control unit, which can also be divided into multiple sub-control units.

In particular, what are controlled/regulated are the actuators, namely in particular the pump/turbine 5, 10, 26 for controlling the flows, the means 24 for clearing (proportions of) respiratory gas, check valves 9, the fresh gas supply (of oxygen) and the anesthetic gas supply.

For the regulation/control of the proportions of specific respiratory gases in a respiratory gas mixture, the control unit takes account of user specifications and/or stored instructions and/or the sensor signals. In particular of at least one flow sensor and/or CO2 sensor and/or O2 sensor and/or anesthetic gas sensor.

Figure 3:
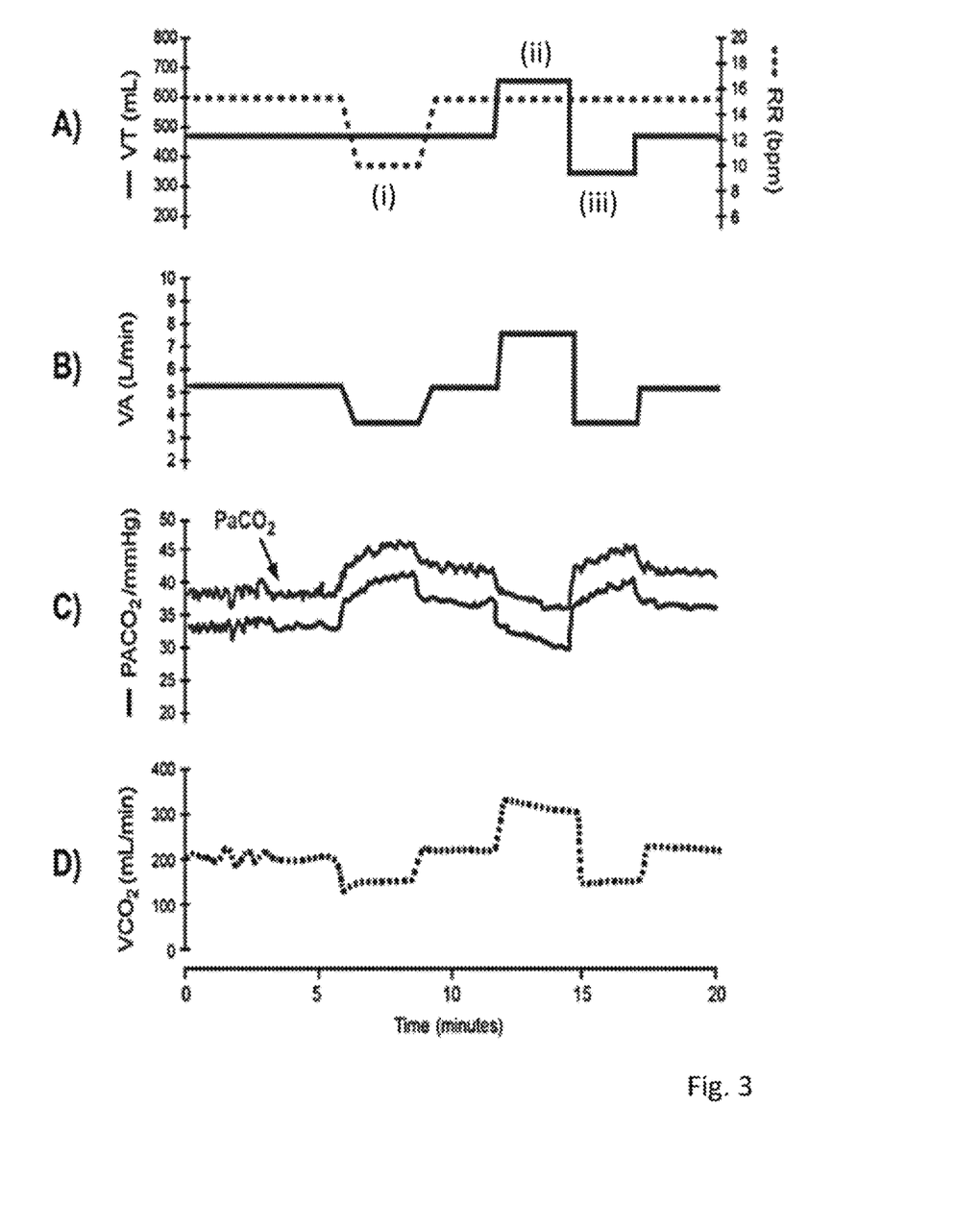
FIG. 3 depicts various graphs illustrating the elimination of carbon dioxide and the partial pressures of alveolar CO2 resulting from implementing a method according to the invention.

FIG. 3 shows the application of the teaching according to the invention (device and method) in a ventilator according to the invention and the implications of the teaching.

FIG. 3 shows the importance of alveolar ventilation VA in eliminating CO2 on a hemodynamically stable, anesthetized patient. FIG. 3 shows the plot of various patient-specific physiological parameters during the monitoring of alveolar ventilation by means of volumetric capnography. (B) depicts the change in alveolar ventilation (VA) in a hemodynamically stable patient through (A) a reduction in respiratory rate (RR) from 15 to 10 breaths per minute (i) and through an increase (ii) and a reduction (iii) in tidal volume (VT) under controlled ventilation.

The elimination of carbon dioxide (VCO2) (depicted in D) and the partial pressures of alveolar CO2 (PACO2) (depicted in C) exhibit opposing behavior. In (C), the partial pressure of arterial CO2 (PaCO2) is plotted above alveolar PACO2 (top line in C).

Not all parts of the airway—from the mouth and nose to the alveoli—are actually involved in gas exchange. In order to be able to assess and, if necessary, optimize the "effectiveness" of ventilation, information about the proportion of "effective" alveolar ventilation is very helpful. Because of its high solubility and the resultant very fast kinetics, CO2 is an ideal indicator for alveolar ventilation (VA). Therefore, the measurement and graphic representation of the partial pressure of CO2 measured in the exhaled gas mixture (PETCO2) in the form of a capnography curve is ideal for the continuous monitoring of ventilation. Examples of the qualitative assessment of ventilation by means of capnography are: disconnection, apnea, exclusion of incorrect intubation, obstruction, exclusion of patient-ventilator asynchrony and much more. Furthermore, PETCO2 is used as a quantitative measure for adjusting ventilation—in the case of stable hemodynamics and constant metabolism, a high PETCO2 is an indicator for hypoventilation and a low PETCO2 is an indication of hyperventilation. In practice, both entail adjustment of the respiratory minute volume (VE) on the ventilator. Since VE is the product of tidal volume and respiratory rate, the modulation of these two components lends itself to this. In principle, low tidal volumes (VT) are striven for nowadays in order to avoid volutrauma, biotrauma and barotrauma by means of lung-protective ventilation. However, what should be particularly borne in mind here is the fact that, with every breath, dead spaces are also ventilated in addition to the alveoli participating in gas exchange. The proportion of this dead space ventilation has a significant influence on the efficiency of ventilation. For respiratory minute ventilation, alveolar ventilation (VA) and dead space ventilation (VD), the following simple formula is applicable:

$$VE = VA + VD$$

VE is therefore composed of an effective portion in which the gas is in contact with the pulmonary capillaries and thus participates in gas exchange (alveolar ventilation=VA) and an ineffective portion which does not participate in gas exchange (dead space=VD). Therefore, VA and its proportion in VE is a measure of the efficiency of breathing, and VA and VD are important characteristic variables for optimizing ventilation settings, especially in the case of people with respiratory limitations. Accordingly, VA is calculated as:

$$VA = VE - VD$$

FIG. 3 shows the importance of VA in eliminating CO2 on a hemodynamically stable, anesthetized patient. Changes in respiratory rate and VT induced changes in VA that have opposing influences on the partial pressures of CO2 and elimination of CO2 (VCO2). The larger VCO2 with increased VA reduces the partial pressures on both sides of the alveolocapillary membrane, which leads to hypocapnia. Conversely, the lower VA entails lower elimination of CO2 and thus hypercapnia.

Capnography is a suitable means for determining and also graphically representing the amount or proportion of expiratory carbon dioxide, or expiratory CO2 for short. The CO2 kinetics of mechanically ventilated patients are represented in a noninvasive way and in real time. Volumetric capnography in particular is a suitable means for the clinical monitoring of mechanically ventilated patients.

By means of capnography, it is possible to measure the concentration of CO2 in respiratory gases over the respiratory cycle. The concentration of CO2 is calculated regularly from the absorption of infrared light according to the Beer-Lambert law and is usually expressed as a partial pressure in the unit mmHg. The graphical representation of the elimination of CO2 during respiration is referred to as a capnogram and the corresponding measurement device is referred to as a capnograph.

The patient-specific physiological parameter of the amount of CO2, or specifically the volume of CO2, which is eliminated in a single patient breath can be determined noninvasively by volumetric capnography by means of integration of the expiratory CO2 over the expiratory tidal volume.

Thus, in the course of the proposed method, the diffusion of CO2 as a patient-specific physiological parameter representing the success of artificial ventilation can be used in order to then automatically make inferences for the adjustment of the at least one technical ventilation parameter. Artificial respiration which is physiologically successful, but also gentle on the patient, can thus be ensured.

According to a further aspect of the teaching, a ventilator for artificial ventilation of a patient is proposed. The proposed ventilator comprises: a measurement device (sensor) which is arranged to measure at least one patient-specific physiological parameter (such as O2 or CO2); a controller which is arranged to define at least one technical ventilation parameter, wherein the patient is ventilated on the basis of the technical ventilation parameter, wherein the at least one technical ventilation parameter corresponds to at least one of the ventilation parameters respiratory gas pressure, respiratory minute volume, tidal volume, respiratory rate, positive end-expiratory pressure, and/or inspiratory oxygen concentration provided by the ventilator, and/or the proportion or partial pressure of CO2 provided by the ventilator; and a regulation unit which is in communication with the measurement device and with the controller. The measurement device is arranged in such a way that it repeatedly measures the at least one patient-specific physiological parameter at time intervals. The regulation unit is arranged in such a way that it adjusts the at least one technical respiration parameter on the basis of the repeat measurement of the patient-specific physiological parameter.

The proposed ventilator for artificial ventilation of a patient is preferably arranged to be operated using an above-described method and/or using the device.

In particular, what is important with respect to the ventilator is recognizing that the functional state of the ventilated lungs, which changes from one breath of the artificially ventilated patient to the next, is incorporated in the regulation of the ventilation settings. A new dimension in ventilation therapy is achieved by the simultaneous incorporation of both technical and physiological characteristic variables, in the form of technical ventilation parameters on the one hand and in the form of patient-specific physiological parameters on the other, in the regulation of the ventilator. This approach allows reliable control of ventilation therapy, even under the worsened conditions to which modern intensive-care medicine is nowadays exposed, namely decreasing patient stays despite increasingly severely ill patients.

The proposed ventilator can automatically observe the patient's state via the patient-specific physiological parameters and automatically adjust the technical ventilation parameters at regular intervals via the proposed regulation/control in such a way that the patient is subjected to artificial ventilation which is successful and also gentle.

According to a further advantageous embodiment of the ventilator, the measurement device is in the form of a capnopgraph and is arranged in such a way that it repeatedly measures the at least one patient-specific physiological parameter by means of capnography, preferably volumetric capnography, and that the at least one patient-specific physiological parameter corresponds to at least one parameter directly representing the CO2 gas exchange in the patient's lungs, preferably at least one of the parameters end-expiratory partial pressure of CO2 in the exhaled gas mixture, alveolar partial pressure of CO2, or eliminated volume of CO2 in a single patient breath.

What is claimed is:

1. A method for separating a respiratory gas mixture which contains at least O2 and CO2 and at least one volatile anesthetic and flows in a respiratory gas path, wherein the method comprises
    guiding the respiratory gas mixture under a first flow to a first separation material which is present in the form of a diffusion filter, where the first separation material separates at least oxygen O2 and carbon dioxide CO2 from the at least one volatile anesthetic, the at least one volatile anesthetic being returned to the respiratory gas path or remaining in the respiratory gas system,
    guiding separated remaining respiratory gas mixture containing at least oxygen O2 and carbon dioxide CO2 under a second flow to a second separation material which is present as a diffusion filter, where the second separation material separates at least carbon dioxide CO2 from the respiratory gas mixture, removed carbon dioxide CO2 being released into the environment or into a respiratory gas scavenging system, and
    returning a remaining portion of the respiratory gas mixture, namely essentially oxygen O2, to the second flow.

2. The method of claim 1, wherein the first separation material selectively allows oxygen O2 and carbon dioxide CO2 to pass through and retains the at least one volatile anesthetic and/or wherein the second separation material selectively allows nitrogen N2 and/or oxygen O2 to pass through and at least largely retains at least carbon dioxide CO2.

3. The method of claim 1, wherein the second separation material is a diffusion filter which has a permeability ratio of N2 and/or O2 to CO2 of at least 50:1.

4. The method of claim 1, wherein the second separation material is a diffusion filter which has a permeability ratio of N2 and/or O2 to CO2 of at least 100:1.

5. The method of claim 1, wherein the first flow and/or the second flow is 4 to 25 l/min.

6. The method of claim 1, wherein the second separation material is a diffusion filter which has a permeability ratio of O2 to CO2 of such a size that the flow of CO2 released into the environment or into the respiratory gas scavenging system is lower than a flush flow of the first separation material.

7. A ventilator, wherein the ventilator is configured for carrying out the method of claim 1 and comprises a device for separating a respiratory gas mixture which contains at least O2 and CO2 and at least one volatile anesthetic and flows in a respiratory gas path, wherein
    the respiratory gas mixture is guided under a first flow to a first separation material which is in the form of a diffusion filter,
    the first separation material separates at least oxygen O2 and carbon dioxide CO2 from the at least one volatile anesthetic,
    the at least one volatile anesthetic is returned to the respiratory gas path or remains in the respiratory gas system,
    the removed remaining respiratory gas mixture containing at least oxygen O2 and carbon dioxide CO2 is guided under a second flow to a second separation material which is in the form of a diffusion filter,
    the second separation material separates at least carbon dioxide CO2 from the respiratory gas mixture,
    the removed carbon dioxide CO2 is released into the environment or into a respiratory gas scavenging system, and
    the remaining portion of the respiratory gas mixture, namely essentially oxygen O2, is returned to the second flow.

8. The ventilator of claim 7, wherein the first separation material is in the form of a diffusion filter in one branch of a respiratory gas hose or in the form of a filter housing comprising an upper inlet for respiratory gas, an upper chamber, an upper outlet for respiratory gas to a patient, a lower chamber and a lower outlet for respiratory gas from the lower chamber to a first respiratory gas path in a direction to the second separation material, and a lower inlet into the lower chamber, coming from a line from the second separation material.

9. The ventilator of claim 8, wherein a flush flow between the lower chamber and a subsequent chamber is regulated according to requirements in such a way that a CO2 content leaving a first stage at the lower outlet is adjustable.

10. The ventilator of claim 8, wherein a no-return valve which selectively prevents a flow of respiratory gas in one direction is disposed in a line between the first separation material and the second separation material.

11. The ventilator of claim 7, wherein the second separation material is in the form of a filter having an upper part and a lower part, wherein a diffusion filter is disposed between the upper and lower parts, wherein the upper part comprises an upper inflow for the respiratory gas mixture which comes from the first separation material, and an upper outflow to the environment, and wherein the lower part comprises a lower outflow to a second respiratory gas path in a direction to the first separation material, a pump or turbine for generating a flush flow for flushing the first separation material being disposed in the second respiratory gas path between the lower outflow and an inflow.

12. The ventilator of claim 7, wherein both diffusion filters are present in the form of film filters and/or surface filters or in the form of tubes and/or hollow fibers, wherein a size of surfaces and of passage cross-sections is configured in such a way that a flow of 60 l/min is possible in a direction of flow and a maximum pressure drop of 2 cmH2O is not exceeded in a direction of diffusion.

13. The ventilator of claim 7, wherein a permeability ratio of N2 and/or O2 to CO2 of the diffusion filter of the second separation material is configured in such a way that CO2 is substantially retained, the permeability ratio being of such a size that the flow of CO2 released into the environment or into a respiratory gas scavenging system is lower than a flush flow in a first stage with the first separation material.

14. The ventilator of claim 7, wherein the device is configured such that in its operation a first flow into the first separation material is from 4 l/min to 30 l/min and a second flow into the second separation material is from 1 l/min to 35 l/min.

15. The ventilator of claim 7, wherein a cascaded flush-flow treatment through the second separation material is provided, the second separation material being in the form of a double or multiple diffusion filter.

16. The ventilator of claim 15, wherein the second separation material separates at least carbon dioxide CO2 from the respiratory gas mixture and segregates it out of an upper chamber via an exit into the respiratory gas scavenging system, a pump returning the segregated carbon dioxide CO2 via a line to an entrance of the second separation material.

17. The ventilator of claim 15, wherein a remaining portion of the respiratory gas mixture that has diffused through a first diffusion filter, namely essentially nitrogen N2 and oxygen O2 is conducted from a lower chamber through an opening to a second diffusion filter through an intake.

18. The ventilator of claim 17, wherein the intake of the second diffusion filter is fed by an outlet of the first diffusion filter, a further reduced proportion of CO2 thus predominating in a lower part of the second diffusion filter and the respiratory gas treated in this way being returned to second flow.

* * * * *